United States Patent
Mäntele et al.

(10) Patent No.: US 10,883,933 B2
(45) Date of Patent: Jan. 5, 2021

(54) NON-INVASIVE SUBSTANCE ANALYSIS

(71) Applicant: DiaMonTech GmbH, Berlin (DE)

(72) Inventors: Werner Mäntele, Kiefersfelden-Mühlbach (DE); Miguel Angel Pleitez Rafael, Frankfurt am Main (DE); Tobias Lieblein, Frankfurt (DE); Otto Hertzberg, Frankfurt (DE); Alexander Bauer, Oberursel (DE); Hermann Von Lilienfeld-Toal, Gelnhausen (DE); Arne Küderle, Frankfurt am Main (DE); Tabea Pfuhl, Dieburg (DE)

(73) Assignee: DiaMonTech AG, Berlin (DE)

( * ) Notice: Subject to any disclaimer, the term of this patent is extended or adjusted under 35 U.S.C. 154(b) by 968 days.

(21) Appl. No.: 15/319,426

(22) PCT Filed: Jun. 16, 2015

(86) PCT No.: PCT/EP2015/063470
§ 371 (c)(1),
(2) Date: Dec. 16, 2016

(87) PCT Pub. No.: WO2015/193310
PCT Pub. Date: Dec. 23, 2015

(65) Prior Publication Data
US 2017/0146455 A1    May 25, 2017

(30) Foreign Application Priority Data
Jun. 16, 2014   (DE) .................. 10 2014 108 424

(51) Int. Cl.
*G01N 21/552*    (2014.01)
*G01N 33/49*    (2006.01)
(Continued)

(52) U.S. Cl.
CPC ......... *G01N 21/552* (2013.01); *A61B 5/1455* (2013.01); *A61B 5/1495* (2013.01);
(Continued)

(58) Field of Classification Search
CPC .... G01N 21/552; G01N 21/171; G01N 33/18; G01N 33/2835; G01N 21/636;
(Continued)

(56) References Cited

U.S. PATENT DOCUMENTS 4,529,319 A    7/1985  Muller
4,790,664 A *  12/1988  Saito .................... G01N 21/171
                                                            356/128
(Continued)

FOREIGN PATENT DOCUMENTS

CN    1555242 A    12/2004
CN    1638690 A    7/2005
(Continued)

OTHER PUBLICATIONS

Farahi et al., "Pump probe photothermal spectroscopy using quantum cascade lasers", Journal of Physics D: Applied Physics, Institute of Physics Publishing Ltd, GB, vol. 45, No. 12, Mar. 6, 2012 (Mar. 6, 2012), p. 125101, XP020219064, ISSN: 0022-3727.
(Continued)

*Primary Examiner* — Eric F Winakur
*Assistant Examiner* — Abid A Mustansir
(74) *Attorney, Agent, or Firm* — Sunstein LLP

(57) ABSTRACT

The invention relates to analyzing a substance. An optical medium is arrange on a substance surface with at least one region of the optical medium surface in contact with the substance surface. An excitation light beam is emitted through the contacting region of the medium surface to the substance surface. A measurement light beam is emitted through the optical medium to the contacting region of the
(Continued)

medium surface such that the measurement light beam and the excitation light beam overlap on the interface of the optical medium and of the substance surface, on which the measurement light beam is reflected. A deflection of the reflected measurement light beam is detected in dependence on the wavelength of the excitation light beam. The substance is then analyzed based on the detected deflection of the measurement light beam in dependence on the wavelength of the excitation light beam.

44 Claims, 5 Drawing Sheets

(51) Int. Cl.
| | |
|---|---|
| *A61B 5/145* | (2006.01) |
| *A61B 5/1455* | (2006.01) |
| *G01N 21/17* | (2006.01) |
| *G01N 21/63* | (2006.01) |
| *A61B 5/1495* | (2006.01) |
| *A61B 5/00* | (2006.01) |
| *G01N 33/18* | (2006.01) |
| *G01N 33/28* | (2006.01) |

(52) U.S. Cl.
CPC ...... *A61B 5/14532* (2013.01); *A61B 5/14546* (2013.01); *A61B 5/443* (2013.01); *G01N 21/171* (2013.01); *G01N 21/636* (2013.01); *G01N 33/18* (2013.01); *G01N 33/2835* (2013.01); *G01N 33/49* (2013.01); *A61B 2560/0223* (2013.01); *A61B 2562/0233* (2013.01); *A61B 2562/0238* (2013.01); *A61B 2562/0242* (2013.01); *G01N 2201/06113* (2013.01)

(58) Field of Classification Search
CPC ......... G01N 33/49; G01N 2201/06113; G01N 21/17; A61B 5/14546; A61B 5/1495; A61B 5/443; A61B 5/14532; A61B 5/1455; A61B 2560/0223; A61B 2562/0233; A61B 2562/0238; A61B 2562/0242
See application file for complete search history.

(56) References Cited

U.S. PATENT DOCUMENTS

| | | | |
|---|---|---|---|
| 4,952,027 | A | 8/1990 | Saito et al. |
| 4,968,144 | A | 11/1990 | Thomas et al. |
| 5,136,172 | A | 8/1992 | Nakata et al. |
| 5,370,114 | A | 12/1994 | Wong et al. |
| 5,513,006 | A | 4/1996 | Schulz et al. |
| 5,574,283 | A | 11/1996 | Quintana |
| 6,332,868 | B1 | 12/2001 | Sato et al. |
| 6,421,548 | B1 | 7/2002 | Berman et al. |
| 6,424,851 | B1 | 7/2002 | Berman et al. |
| 6,484,044 | B1 | 11/2002 | Lilienfeld-Toal |
| 7,133,710 | B2 | 11/2006 | Acosta et al. |
| 7,215,982 | B2 | 5/2007 | Oshima et al. |
| 7,215,983 | B2 | 5/2007 | Cho et al. |
| 7,262,836 | B2 | 8/2007 | Uchida et al. |
| 7,438,855 | B2 | 10/2008 | Sota et al. |
| 9,255,841 | B2 | 2/2016 | Witinski et al. |
| 9,554,735 | B2 | 1/2017 | Rebec et al. |
| 9,784,620 | B2 | 10/2017 | Witinski et al. |
| 9,833,179 | B2 | 12/2017 | Ikeda |
| 2006/0043301 | A1* | 3/2006 | Mantele ............... G01N 21/85 250/339.11 |
| 2006/0281982 | A1 | 12/2006 | Grata et al. |
| 2009/0247843 | A1 | 10/2009 | Xu |
| 2011/0109907 | A1* | 5/2011 | Meyers ............... G01N 21/552 356/445 |
| 2013/0150691 | A1* | 6/2013 | Pace ................... A61B 5/0004 600/347 |
| 2013/0248690 | A1* | 9/2013 | Van Den Eerenbeemd ................ G02B 13/22 250/208.1 |
| 2013/0286397 | A1 | 10/2013 | Witinski et al. |
| 2015/0192461 | A1 | 7/2015 | Chen |
| 2017/0014057 | A1 | 1/2017 | Sato |
| 2017/0115206 | A1* | 4/2017 | De Boer ............ G01N 21/0303 |
| 2017/0146455 | A1 | 5/2017 | Mäntele et al. |
| 2018/0348053 | A1 | 12/2018 | Koide |

FOREIGN PATENT DOCUMENTS

| | | |
|---|---|---|
| CN | 101263388 A | 9/2008 |
| CN | 104541193 A | 4/2015 |
| DE | 4446390 C1 | 7/1996 |
| DE | 10 2005 048 807 B3 | 11/2006 |
| DE | 10 2014 108 424 B3 | 6/2015 |
| EP | 427943 A1 | 5/1991 |
| EP | 1 048 265 A1 | 11/2000 |
| JP | S6363945 | 3/1988 |
| JP | H03-156362 A | 7/1991 |
| JP | 2846079 B2 | 1/1999 |
| JP | 2000-204904 A | 7/2000 |
| JP | 2000-232970 A | 8/2000 |
| JP | 3594534 B2 | 9/2004 |
| JP | 4052461 B2 | 11/2004 |
| JP | 2005-127748 | 5/2005 |
| JP | 2005-535411 | 11/2005 |
| JP | 2006-242816 A | 9/2006 |
| JP | 2007-242747 A | 9/2007 |
| JP | 2008-107098 A | 5/2008 |
| JP | 2008125542 A | 6/2008 |
| JP | 2005-543437 A | 12/2008 |
| JP | 2009-219800 A | 10/2009 |
| JP | 2012-070907 | 4/2012 |
| JP | 2012-119409 A | 6/2012 |
| JP | 4963482 B2 | 6/2012 |
| JP | 5628008 B2 | 11/2014 |
| JP | 6387610 B2 | 7/2015 |
| JP | 6201315 B2 | 9/2017 |
| RU | 135139 U1 | 11/2013 |
| WO | WO 95/31133 | 11/1995 |
| WO | WO 1996031765 A1 | 10/1996 |
| WO | WO 00/21437 | 4/2000 |
| WO | WO 2003100393 A1 | 12/2003 |
| WO | WO 2004/016171 A1 | 2/2004 |

OTHER PUBLICATIONS

Guo et al., "Non-invasive Glucose Measurements Using Wavelength Modulated Differential Photothermal Radiometry (WM-DPTR)", International Journal of Thermophysics, Aug. 24, 2012 (Aug. 24, 2012), XP055211861, ISSN: 0195-928X, DOI: 10.1007/s10765-012-1276-z.

George et al., "Fibre optic position sensitive detection of photothermal deflection", Applied Physics B: Lasers and Optics, vol. 77, No. 1, Aug. 20, 2003 (Aug. 20, 2003), pp. 77-80, XP055211868, ISSN: 0946-2171, DOI: 10.1007/S00340-003-1117-7.

Fujinami et al., Highly sensitive detection of molecules at the liquid/liquid interface using total internal reflection-optical beam deflection based on photothermal spectroscopy; Review of Scientific Instruments, vol. 74, No. 1, Jan. 2003, 352-354.

International Searching Authority—EPO, International Search Report and Written Opinion, PCT/EP2015/063470; dated Sep. 18, 2015. 12 pages.

International Searching Authority/European Patent Office, International Search Report, Application No. PCT/DE2015/200532, dated May 17, 2016, 3 pages.

International Searching Authority/European Patent Office, International Search Report, Application No. PCT/EP2016/080046, dated Mar. 24, 2017, 3 pages.

(56) References Cited

OTHER PUBLICATIONS

Kawazumi et al., *Development of an interfacial thermal lens technique: monitoring the dissolving process of amphiphilic molecules at the hexane-water interface*, Chemical Physics Letters, vol. 282, 1998, pp. 159-163.
Naoki Wadamori et al., *Determination of Measurable Depth Based on Optical Modulation Frequency by Photoacoustic Spectroscopy*, Transactions of Japanese Society for Medical and Biological Engineering, vol. 49, No. 1 (2011), pp. 220-225 (with English abstract).
Naoki Wadamori et al., *Determination of Measurable Depth Based on Optical Modulation Frequency by Photoacoustic Spectroscopy*, Transactions of Japanese Society for Medical and Biological Engineering, vol. 49, No. 1 (2011), pp. 220-225 (with English translation).

\* cited by examiner

NON-INVASIVE SUBSTANCE ANALYSIS

CROSS-REFERENCE TO RELATED APPLICATIONS

This Application is a U.S. national stage entry under 35 USC § 371 of PCT/EP2015/063470 filed Jun. 16, 2015, which claims priority to German Patent Application 10 2014 108 424.1, filed Jun. 16, 2014; both of which are incorporated herein by reference in their entireties.

FIELD OF THE INVENTION

The present invention relates to a method and a system for analyzing a substance non-invasively. In particular, it relates to a method and a system for non-invasively analyzing a substance from the deflection of a probe light beam which is reflected in an optical medium placed on the substance.

BACKGROUND

In a wide variety of technical applications and in particular in chemical, biological and medical applications, the analysis of substances is required with regard to their composition and their constituent substances. In many of the analysis methods, part of the substance is removed and made to react with other substances. From the change in the reaction mixture, conclusions can then be drawn as to the constituent substances of the substance.

The removal or alteration of the substance can be undesirable however, for example if as a result of the reaction the substance is no longer usable for its actual purpose, or if the removal of a part of the substance damages or destroys the substance. In these cases, a non-invasive substance analysis can be advantageous, in which the original function or application capability of the substance is not adversely affected by the analysis.

SUMMARY OF THE INVENTION

The object of the present invention is therefore to provide a method and a system for the non-invasive analysis of a substance.

This problem is solved by a method according to claim 1 and a system according to claim 28. Preferred embodiments are disclosed in the dependent claims.

According to the invention, the method comprises a step of arranging an optical medium on a substance surface, so that at least a portion of the surface of the optical medium is in contact with the substance surface. In the context of the present invention, the step of arranging the optical medium on a substance surface shall in particular be understood to also include the arrangement of a substance surface on the optical medium, and in general any bringing into contact thereof. Thus the optical medium can also be designed in particular as a holder for a substance, or be fixedly connected to a substance. Preferably, the optical medium is a body made of ZnS, ZnSe, Ge or Si, which is transparent in a predetermined wavelength range, preferably in the infrared range or a part of the infrared range. The substance can be a tissue, for example skin, but also a liquid or a solid or a combination of solid, skin and tissue, such as a sample holder made of glass with either a tissue to be examined located thereon or a liquid contained therein.

The aforementioned contact typically involves a direct contact. A "direct contact" is considered to be one in which the surfaces of the optical medium and the substance are touching. In this regard, the above step of arranging the optical medium on the substance surface means bringing the surfaces of the optical medium and the substance into contact. For example, the optical medium and the substance can each have (substantially) flat surfaces in one region, which are brought into contact with each other.

The method according to the invention also comprises the step of emitting an excitation light beam with an excitation wavelength through the region of the surface of the optical medium, which is in contact with the substance surface, onto the substance surface. In addition, the method according to the invention comprises the step of emitting a probe light beam through the optical medium onto the region of the surface of the optical medium which is in contact with the substance surface, in such a way that the probe light beam and excitation light beam overlap at the interface of the optical medium and the substance surface. Preferably, the probe light beam and excitation light beam overlap at the interface of the optical medium and the substance surface by 10% to 100% or 50% to 100%, particularly preferably by more than 90%, or even by 100%. The degree of overlap is determined, for example, by the fact that a first interface region is defined in which 95%, preferably 98%, of the total light intensity of the probe light beam is located. Similarly, a second interface region is defined in which between 95% and preferably 98% of the total light intensity of the excitation light beam is located. The intersection of the first and second interface regions is then divided by the mean of the first and second interface regions to give the degree of overlap.

The method according to the invention also includes the step of directly or indirectly detecting a deflection of the reflected probe light beam as a function of the wavelength of the excitation light beam. The deflection can be determined, for example, directly by means of a position-sensitive photo detector (PSD) or indirectly by means of a photo-detector, in particular a photodiode, which is arranged behind an iris diaphragm.

Furthermore, the method according to the invention comprises the step of analyzing the substance on the basis of the detected deflection of the reflected probe light beam as a function of the wavelength of the excitation light beam. 'Analyzing' here means, in particular, measuring or determining parameters which characterize the substance composition. Preferably, the analysis comprises determination of an absorption characteristic of the substance. If the excitation light beam is an infrared light beam, then the analysis preferably includes performing an infrared spectroscopy measurement.

The method according to the invention is based on the fact that an excitation light beam absorbed in a substance changes the beam path of a probe light beam through the optical medium. The reason for this is that the absorption of the excitation light beam in the substance induces a temperature increase, which locally changes the refractive index or index of refraction of the optical medium in contact with the substance, and thus deflects the beam path of the probe light beam. The degree of deflection correlates with the degree of absorption of the excitation light beam in the substance, so that substance components with characteristic absorption spectra can be identified from the degree of deflection of the probe beam.

The method preferably comprises the step of aligning the probe light beam, so that the probe light beam undergoes total internal reflection at the interface between the optical medium and the substance surface. The term "total internal" reflection in this description and the claims, in accordance with Snell's law of refraction, is equated with an angle of incidence of the probe light beam that is greater than the critical angle of total internal reflection, which is equal to the arcsine of the quotient of the refractive index of the substance divided by the refractive index of the optical medium. The probe light beam is preferably aligned such that it enables the analysis of a plurality of different substances with different optical densities.

The excitation light beam is preferably designed as an intensity-modulated, in particular pulsed, excitation light beam. The modulation frequency, in particular the pulse rate, is preferably between 5 and 2000 Hz and particularly preferably between 10 and 1000 Hz, or 20 and 700 Hz. If the excitation light beam is designed as a pulsed-excitation light beam, the cyclic heating and cooling of the excitation light-absorbing substance constituents generates expansion and contraction of the constituents and hence pressure waves, and in particular thermal waves, which pass through the substance and propagate into the optical medium and thus also deflect the beam path of the probe light beam.

Preferably, the step of emission of the excitation light beam is repeated for different modulation frequencies and the step of analyzing the substance comprises the analysis of the substance on the basis of the detected deflections of the probe light beam as a function of the wavelength and the modulation frequency of the excitation light beam. In doing so, different modulation frequencies allow different layers to be included in the absorption process. Thus, for example, higher modulation frequencies lead to absorption processes nearer to the surface, while lower modulation frequencies also include absorption processes in deeper layers. Thus, an analysis of different layers is facilitated.

The step of analyzing the substance preferably comprises subtracting a value which is based on a deflection of the probe light beam that was detected at a first modulation frequency from a value based on a deflection of the probe light beam that was detected at a second modulation frequency, or dividing a value based on a deflection of the probe light beam that was detected at a first modulation frequency, by a value based on a deflection of the probe light beam that was detected at a second modulation frequency. By calculating the difference or performing the division, the influence of superficial layers can then be deduced by calculating absorption processes which occur in superficial and deeper layers, so that the contribution of the deeper layers can be determined.

The step of analyzing the substance preferably comprises a subtraction of values which are based on deflections of the probe light beam that were detected at a first modulation frequency for different wavelengths of the excitation light beam, from values which are based on deflections of the probe light beam that were detected at a second modulation frequency for different wavelengths of the excitation light beam, wherein the values are particularly preferably spectral absorption intensity values, or a division of values based on deflections of the probe light beam which were detected at a first modulation frequency for different wavelengths of the excitation light beam, by values based on deflections of the probe light beam which were detected at a second modulation frequency for different wavelengths of the excitation light beam, wherein the values are preferably spectral absorption intensity values. By subtracting or dividing the values, an absorption spectrum of a particular layer of the material can be isolated, so that the presence of certain substances in this layer can be demonstrated, which is particularly advantageous when the occurrence of the substances is not evenly distributed in the material.

The step of analyzing preferably comprises associating values, which are based on deflections of the probe light beam which were detected at different modulation frequencies, to different regions in the substance, preferably regions of the substance located at different depths. By assigning or associating the values with substance regions, a distribution of a substance in the containing substance can be provided, in particular a depth profile of the presence of a particular substance.

The determination of the deflection of the probe light beam preferably comprises the amplification of an associated probe signal with a lock-in amplifier. By the use of a pulsed-excitation light beam in combination with a lock-in amplifier, even small signals or signal changes which lie within the noise range can also be rendered detectable. The pulsed excitation light beam is preferably modulated by an optical chopper. The optical chopper is preferably coupled to the lock-in amplifier. Alternatively, the pulsed-excitation light beam can be generated by a pulsed-excitation light source.

Preferably, the excitation light beam is focussed on the surface of the optical medium by means of an optical device, wherein the optical device in particular comprises a parabolic mirror. The optical device is preferably adjusted by means of an adjustment laser, which emits visible light. The laser beam of the adjustment laser can be adjusted or aligned by means of a mirror arrangement such that the beam path of the adjustment laser beam is at least partly coincident with the beam path of the excitation light beam.

The wavelength of the excitation light beam is preferably varied, in particular by the wavelength being cyclically tuned within a predetermined wavelength range or by characteristic wavelengths, in particular absorption wavelengths of a suspected substance, being selectively set. The variation of the wavelength range of the excitation light beam enables a spectral analysis to be performed, which allows substance constituents with partially similar or overlapping absorption spectra to be differentiated. The variation of the predetermined wavelength range can be effected, for example, using a tuneable light source.

The excitation light beam is preferably an excitation laser beam. Due to the use of an excitation laser beam, the absorption range or an absorption spectrum can be analyzed with high resolution. For the infrared spectral range, a quantum cascade laser can preferably be used as an excitation laser.

The probe light beam is preferably a probe laser beam. The wavelength of the probe light beam is preferably in the visible wavelength range. The use of a visible probe laser beam enables a simplification of the alignment of the probe laser beam onto the region of the interface through which the excitation light beam passes.

The excitation wavelength is preferably in a range from 6 µm to 13 µm, particularly preferably from 8 µm to 11 µm.

The polarization of the probe beam is preferably adjusted such that the deflection of the reflected probe light beam is a maximum.

Before detection of the deflection, the probe light beam preferably undergoes total internal reflection at the same point at the interface of the optical medium at least one more time, preferably two to five more times. For example, by the probe light beam being reflected back by a mirror system onto the region of overlap with the excitation light beam. This effectively increases the deflection angle, allowing the accuracy of detection of the deflection to be increased.

If the substance to be analyzed is the skin of a patient, the method preferably comprises the step of preparing the surface of the skin by applying and removing a fabric strip to remove dead skin cells, wherein the fabric strip comprises a substance which adheres to the surface of the skin. The removal of the dead skin cells enables the analysis accuracy to be improved, because interfering effects due to dead skin cells can be avoided.

If the substance to be analyzed is the skin of a patient, the step of analyzing the substance preferably comprises the step of determining the blood sugar level of the patient. The step of determining the blood sugar level particularly preferably comprises the step of measuring the glucose content of the interstitial fluid of the skin of the patient.

If the substance to be analyzed is the skin of a patient, the step of analyzing the substance preferably comprises the step of determining a water content of the skin of the patient.

If the substance to be analyzed is the skin of a patient, the step of analyzing the substance preferably comprises the step of determining a protein composition of the skin of the patient, and particularly preferably determining a protein composition of the skin of the patient in different layers of the skin. It is understood that the term "skin layers" should be understood as meaning regions in the skin that extend (substantially) parallel to the skin surface and are located above or underneath each other.

Preferably, the substance is a fluid or stationary fluid or emulsion and the analysis of the substance comprises determining a sugar content, alcohol content, fat and/or protein content of the fluid.

The substance is preferably a fuel and the analysis of the substance comprises determining an alcohol content, rapeseed oil methyl ester content, lead or benzene content of the fuel.

The substance is preferably fresh water or salt water and the analysis of the substance comprises determining a contamination of the water.

Preferably, the substance is a body fluid.

Based on the detected deflection of the probe light beam, an absorption intensity value is preferably associated with the wavelength of the excitation light beam. The absorption intensity value can be compared with a calibration absorption intensity value, which represents the absorption intensity value of the skin of the patient with a known blood sugar level and at this exact wavelength of the excitation light beam. The current blood sugar level of the patient is then preferably determined on the basis of the comparison, wherein the determined blood sugar level deviates the more from the blood sugar level on which the calibration is based, the more the absorption intensity value deviates from the calibration absorption intensity value.

The system according to the invention comprises an optical medium, a device for emitting one or more excitation light beams with an excitation wavelength, and a measurement device. As already discussed above, the optical medium can be, for example, a body made of ZnS, ZnSe, Ge or Si, which is transparent in a predetermined wavelength range.

The device for emitting the excitation light beam is arranged such that the excitation light beam emitted enters into the optical medium through a first surface and leaves it again through a predetermined point on a second surface. If a substance is arranged at the second interface of the optical medium, the excitation light beam is at least partially absorbed on the surface of the substance or in the substance. The degree of absorption can be detected with a measurement device.

The measurement device comprises a device for emitting a probe light beam, which is arranged such that during operation, an emitted probe light beam enters into the optical medium and overlaps with the excitation light beam at the interface of the optical medium and the substance surface. The probe light beam and excitation light beam preferably overlap at the interface of the optical medium and the substance surface by 10% to 100%, or 50% to 100%, particularly preferably by more than 90% or even by 100%. As described above, the degree of overlap is determined, for example, by the fact that a first interface region is defined on which 95%, preferably 98%, of the total light intensity of the probe light beam is located. Similarly, a second interface region is defined in which between 95%, preferably 98% of the total light intensity of the excitation light beam is located. The intersection of the first and second interface regions is then divided by the mean of the first and second interface regions to give the degree of overlap.

For example, the probe light beam can impinge on the interface between the second surface and substance surface at an angle that is smaller than the critical angle of total internal reflection, wherein the point of incidence overlaps with the point of incidence of the excitation light beam and is preferably coincident with it.

The measurement device additionally comprises a device for receiving the reflected probe light beam and for directly or indirectly detecting a deflection of the reflected probe light beam.

If, for example, the optical medium is arranged with the second surface on a substance to be analyzed, then the excitation light beam enters into the substance and, depending on the composition of the substance and the wavelength of the excitation light beam, is absorbed by differing amounts. The absorption of the excitation light triggers heat transport and pressure waves, which affect the beam path of the probe laser beam in the optical medium. Since the effect is correlated with the concentration of a substance constituent absorbing the infrared light, the concentration of the substance constituent can be determined by measuring the degree of deviation in the beam path from an unaffected beam path.

In operation, the probe light beam preferably undergoes total internal reflection at the interface between the optical medium and the substance surface.

The excitation light beam is preferably an infrared light beam, since infrared light is characteristically absorbed by many substances and is therefore particularly suitable for substance analysis.

The excitation light beam is preferably an intensity-modulated, in particular pulsed, excitation light beam. The device for receiving the reflected probe light beam and for directly or indirectly detecting the deflection of the reflected probe light beam preferably comprises a lock-in amplifier. The modulation frequency, in particular the pulse rate, is preferably between 5 and 2000 Hz, particularly preferably between 10 and 1000 Hz, or 20 and 700 Hz. In order to generate a pulsed-excitation light beam the device for emitting the excitation light beam preferably comprises an optical chopper. The optical chopper is preferably positioned in the beam path of the excitation light beam and modulates the intensity of the excitation light beam. The use of an intensity-modulated, and in particular a pulsed light beam in combination with a lock-in amplifier, means that small signals or signal changes which lie within the noise range, can also be detected.

The excitation light beam is preferably an excitation laser beam, and the device for emitting the excitation laser beam is configured for emitting excitation laser beams of different excitation frequencies. Due to the use of an excitation laser beam, the absorption region, or an absorption spectrum, can be analyzed with high resolution.

Preferably, the system also comprises an optical device which is intended for focussing the excitation light beam at the predetermined point. By focusing on the predetermined point, the effect of the excitation light beam can be concentrated even more strongly, causing the deflection of the probe beam to be even greater. The optical device may comprise, for example, a parabolic mirror.

The system preferably comprises an adjustment laser, which facilitates the adjustment of the optical device. The system in this case preferably comprises a mirror pair, which is suitable for adjusting or aligning the beam path of the adjustment laser in such a way as to ensure that at least a portion of the adjustment laser beam is coincident with the beam path of the excitation light beam.

The device for emitting the excitation light beam is preferably a quantum cascade laser. The device for emitting the excitation light beam is preferably tuneable in an excitation wavelength range of 6 µm to 13 µm, preferably 8 µm to 11 µm.

The wavelength of the probe light beam is preferably in the visible range. This simplifies the alignment of the probe light beam to the excitation light beam.

The device for receiving the reflected probe beam and for directly or indirectly detecting the deflection of the reflected probe light beam preferably comprises a photo-detector, in particular a photodiode, and an iris diaphragm, wherein the photo-detector is arranged behind the iris diaphragm, or a PSD.

Before detection of the deflection, the probe light beam preferably undergoes total internal reflection at the same point at the interface of the optical medium at least one further time, preferably two to five more times. For example, by the probe light beam being reflected back by a mirror system at a different angle onto the point of overlap with the excitation light beam. Due to the multiple reflections in the overlap region, the deflection angle is effectively increased, which increases the accuracy of detection of the deflection.

Furthermore, the method and the system are designed for analyzing substances both on and in the skin, and for recording depth-selective profiles of these substances. The method and system are both also suitable for the analysis of traces of substances, such as contaminants or explosives, on the skin. Or for investigating the absorption of cosmetics into the skin, such as fats and ingredients of creams, ointments or lotions, or of pharmaceutical active ingredients, medicines etc. The method and system are also suitable for sensing-related applications, such as monitoring flowing and standing liquids or solutions and emulsions, for determining such properties as their alcohol content or the composition of alcoholic beverages such as beer, wine or spirits, the fat content of milk or milk products, and in general the sugar, fat, alcohol or protein content of foodstuffs. In addition, the method and system are suitable for fuel analysis, for example for determining levels of lead or benzene, measurement of water pollutants (e.g. oil) or the analysis of body fluids and the analysis of pathological and non-pathological changes in the skin, such as the detection of melanoma by determination of the protein composition of the skin at various skin depths, the detection of psoriasis or allergies, and the determination of skin moisture content.

The system is preferably comprised in an apparatus for determining the blood sugar level of a patient, which apparatus also comprises a controller for setting different wavelengths of the excitation light beam and a logic unit or calculation unit, which is configured for determining the blood sugar level in the skin of a patient from detected deflections of the probe beam as a function of the excitation wavelength, when the optical medium is brought into contact with the skin of the patient in such a way that the excitation light beam emerging from the optical medium at the predetermined point enters into the skin.

The system is preferably comprised in an apparatus for analyzing a substance, which device also comprises a controller for setting different modulation frequencies of the excitation light beam and a logic unit or calculation unit, which is configured for analyzing the substance by means of the detected deflections of the probe light beam at different modulation frequencies, when the optical medium is brought into contact with the substance in such a way that the excitation light beam emerging from the optical medium at the predetermined point enters into the substance.

The substance is preferably the skin of a patient and the logic unit or calculation unit is configured for analyzing different layers of the skin of the patient from detected deflections of the probe light beam at different modulation frequencies.

The system is preferably comprised in an apparatus for determining ingredients of a liquid or emulsion, which apparatus also comprises a controller for setting different wavelengths of the excitation light beam and a logic or calculation unit, which is configured for determining ingredients of the liquid or emulsion from detected deflections of the probe beam as a function of the excitation wavelength, when the optical medium is brought into contact with the liquid or emulsion in such a way that the excitation light beam emerging from the optical medium at the predetermined point enters into the liquid or emulsion.

SHORT DESCRIPTION OF THE FIGURES

Figure 6A:
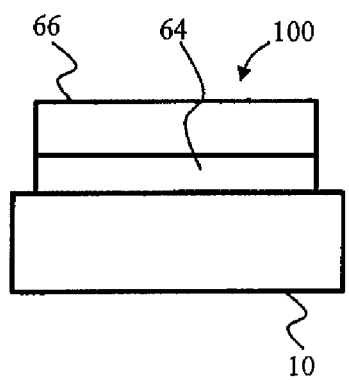
Figure 6B:
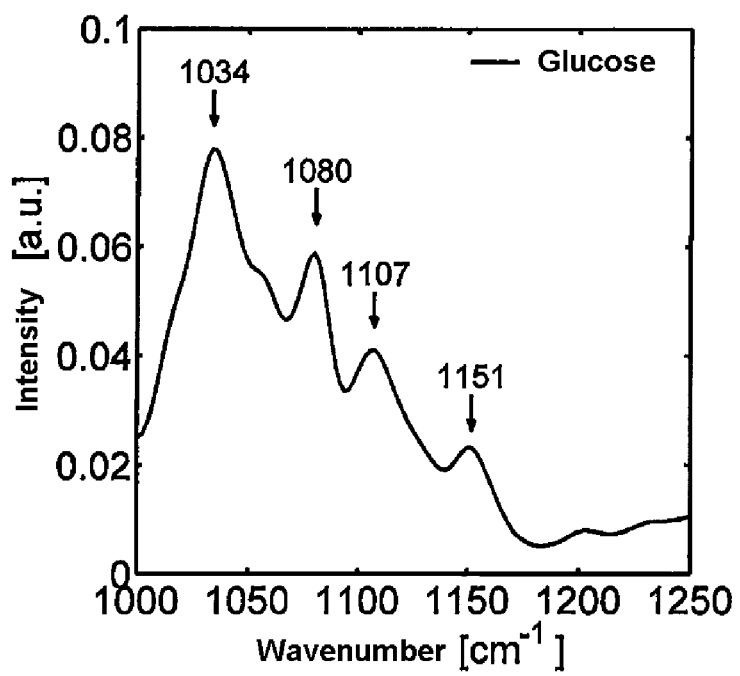
Figure 6C:
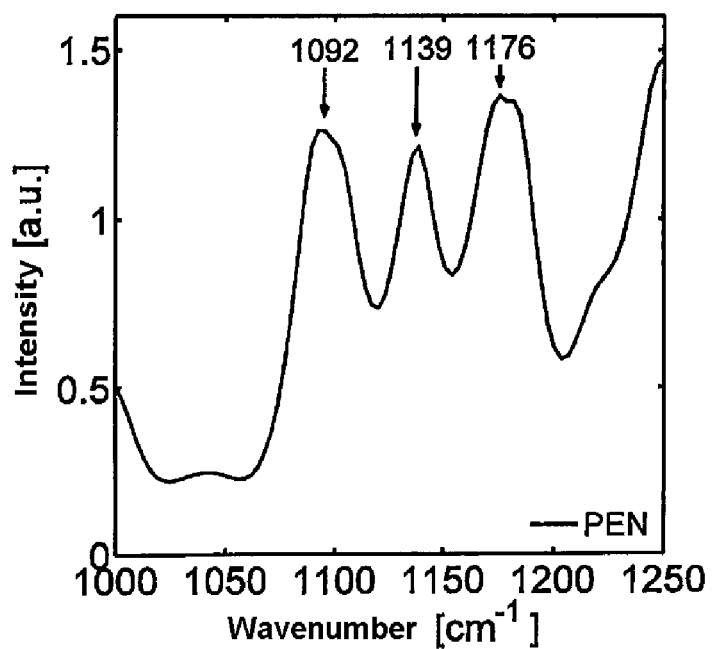
Figure 7:
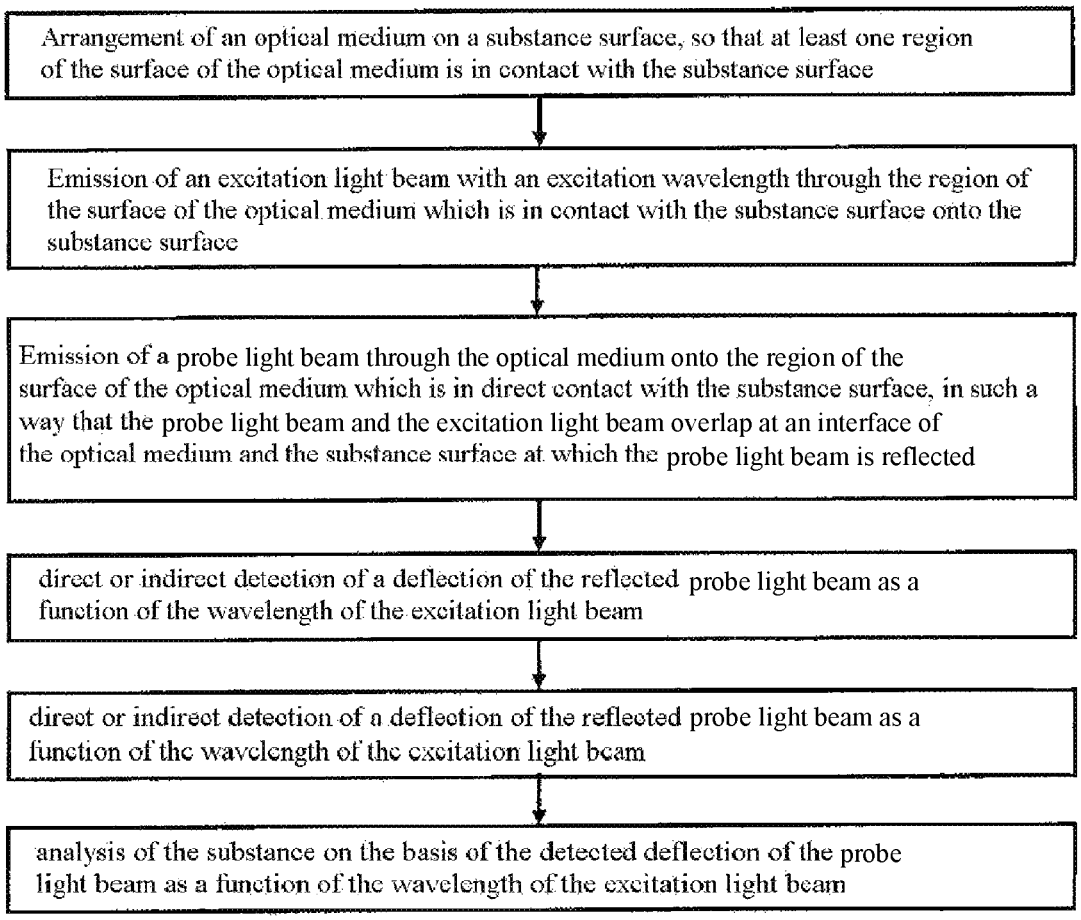

FIG. 6a-c show a schematic representation of a substance to be analyzed, the absorption intensity spectrum of glucose, and the absorption intensity spectrum of a polymer layer;

FIG. 7 shows process steps of the method according to the invention.

DESCRIPTION OF PREFERRED EXEMPLARY EMBODIMENTS

Figure 1:
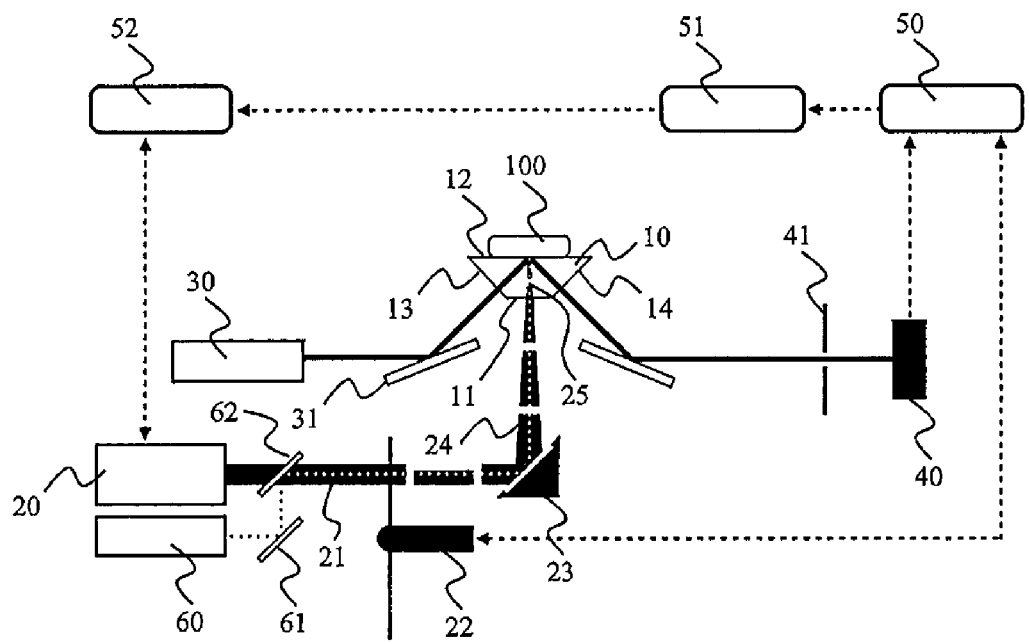
FIG. 1 shows a schematic representation of a preferred exemplary embodiment of the system according to the invention in operation.

FIG. 1 shows a schematic representation of a preferred exemplary embodiment of the system according to the invention in operation. The preferred exemplary embodiment comprises an optical medium 10, a device for emitting an infrared light beam in the form of a quantum cascade laser 20, a device for emitting a probe light beam in the form of a probe laser 30 and a device having means for receiving the reflected probe laser beam with a photodiode 40 and having means for evaluating the reflected probe laser beam, which comprise a lock-in amplifier 50, a digital-to-analogue converter 51 and a computer 52.

The quantum cascade laser 20 transmits an infrared laser beam on a first infrared laser beam sub-path 21 through an optical chopper 22, which converts the continuous infrared laser beam into a pulsed infrared laser beam, preferably with a pulse frequency of between 10 Hz to 1000 Hz. Alternatively, the device for emitting the infrared light beam, here the quantum cascade laser 30, can be operated in pulsed mode—also with a pulse frequency of preferably 10 Hz to 1000 Hz.

At the end of the first infrared laser beam sub-path 21, the infrared laser is incident on a parabolic mirror 23. The parabolic mirror 23 diverts the infrared laser beam along a second infrared laser beam sub-path 24 onto a first surface 11 of the optical medium 10. In the preferred exemplary embodiment shown in FIG. 1, the angle of incidence between the second infrared laser beam sub-path 24 and the first surface 11 has the value 90°. In principle however, other angles of incidence between the second infrared laser beam sub-path 24 and the first surface 11 are also possible, provided the infrared laser beam enters into the optical medium 10 through the first surface 11 and is not totally internally reflected.

The beam path of the infrared laser beam passes along a third infrared laser beam sub-path 25 in the optical medium 10 towards a second surface 12 of the optical medium 10. In the preferred embodiment shown in FIG. 1, the angle of incidence between the third infrared laser beam sub-path 25 and the second surface 12 has the value 90°. In principle however, other angles of incidence between the third infrared laser beam sub-path 25 and the second surface 12 are also possible, provided a sufficient proportion of the infrared laser beam can exit the optical medium 10 through the second surface 12.

In the preferred embodiment shown in operation in FIG. 1, the infrared laser beam penetrates along a fourth infrared laser beam sub-path into a substance sample 100, which abuts against the optical medium 10. The distance between the parabolic mirror 23 and the second surface 12 of the optical medium and the shape of the parabolic mirror 23 are selected, taking into account the optical densities along the second and third infrared laser beam sub-path 24, 25, such that the infrared laser beam is focused onto the second surface 12, or onto a point which is located at a predetermined distance, e.g. between 30 µm and 100 µm, behind the second surface 12 in the substance sample 100.

In the substance sample the infrared laser beam is at least partially absorbed by substance constituents. The absorption changes the temperature of the absorbing substance constituent. In the case of a pulsed infrared laser beam as shown in FIG. 1, pressure and thermal waves are generated, since the absorbing substance components are cyclically heated up and cooled down and the resulting expansion fluctuations give rise to pressure fluctuations, which propagate through the substance in the form of pressure waves. Since the optical medium 10 and the substance are in direct contact, the thermal and pressure waves that are generated migrate into the optical medium 10, where they affect the refractive index.

The measurement of the absorption of the infrared laser beam and the change in the optical density of the optical medium 10 correlated with the absorption is performed by the probe laser beam emitted by the probe laser 30. In FIG. 1 the probe laser beam is directed onto a third surface 13 of the optical medium 10 by way of a first mirror 31. Alternatively, the probe laser 30 can also be aligned such that the probe laser beam is directed directly onto the third surface 13. As shown in FIG. 1, the beam path of the probe laser beam can include an angle of 90° with the third surface 13. Alternatively, the beam path of the probe laser beam can include a smaller angle with the third surface 13, provided a sufficient component of the probe beam can enter into the optical medium 10.

However, the beam path of the probe beam must be adjusted or aligned such that the point of incidence of the probe laser beam on the second surface 12 of the optical medium 10 is coincident with the point of incidence of the infrared light beam on the second surface 12 of the optical medium, or at least overlaps it. This ensures that during operation of the infrared laser beam, the beam path of the probe laser beam passes through the above described region of the optical medium 10, in which the refractive index n is sufficiently strongly influenced by the absorption of the infrared laser beam in the substance 100, wherein it is clear that this region is limited, since the pressure waves are attenuated as they propagate and the heat increase decreases with distance from the absorption region.

Preferably, the optical density of the optical medium 10 is selected in accordance with the substance 100 to be examined and with the angle between the beam path of the probe laser beam and the second surface 12, such that the probe laser beam is totally internally reflected at the second surface 12, or at the interface between the second surface 12 of the optical medium 10 and the substance 100. In the subsequent course of the beam path the reflected, or totally internally reflected, probe laser beam is incident on a fourth surface 14 of the optical medium 10. The fourth surface 14 is such that the probe laser beam exits the optical medium 10 through the fourth surface 14.

As shown in FIG. 1, the probe laser beam which exits the optical medium 10 is detected by the photodiode 40. The deflection of the probe laser beam due to the change in the optical density in a sub-region of the optical medium 10 can be measured, as shown in FIG. 1, by the fact that the probe laser beam passes through an iris diaphragm 41 before being incident on the photodiode 40. The deflected probe laser beam is then partially impeded by the iris diaphragm 41 from being incident in the photodiode 40, so that the intensity of the probe laser beam as measured at the photodiode 40 decreases due to the deflection caused upon traversing the optical medium 10. Alternatively, a spatially resolving photodiode 40, for example, a four-quadrant photodiode, can be used to measure the change in the beam path, or deflection. In this case, the iris diaphragm 41 can be omitted.

The lock-in amplifier 50 receives the signal from the photodiode 40 and the frequency signal of the pulsed infrared light beam. The lock-in amplifier filters out the noise from the intensity signal, so that even small intensity fluctuations can be measured.

The filtered intensity signal of the photodiode 40 is converted by means of a digital-to-analogue converter 51 into a digital signal and transmitted to a computer 52, which is configured for recording the intensity measurements as a function of the wavelength, or wavelength range, of the quantum cascade laser 30 and for comparing the recorded values with a calibration curve, in order to derive conclusions as to the composition of the substance 100. The computer 52 for this purpose comprises a processor, a storage unit and instructions, which, when they are executed by the processor, record the intensity measurements in association with the wavelength or wavelength range of the quantum cascade laser 30.

The process described above, an overview of which is shown in FIG. 7, is preferably repeated for a series of different wavelengths or wavelength ranges in the infrared light range, to enable the absorption spectrum of individual or a plurality of substance constituents to be determined. In doing so, the presence of a substance constituent can be determined by measuring characteristic absorption spectra, and the concentration of the substance constituent can be determined from the amplitude of the spectrum, for example by comparison with a calibration curve. For this purpose the quantum cascade laser 30 can be tuneable, for example, in the wavelength range of 8 µm to 11 µm.

If the system is used to determine a blood sugar value of a patient, the blood sugar level of the patient can be calculated from the measured absorption spectrum of the glucose in the interstitial fluid by means of a calibration curve.

The system shown in FIG. 1 comprises a device for emitting an adjustment or alignment laser beam, here in the form of an He—Ne laser 60, and a mirror pair 61, 62, which aligns the beam path of the adjustment laser such that at least a portion of the beam path of the adjustment laser is coincident with the beam path of the infrared light beam, i.e. the excitation light beam.

If the substance 100 to be analyzed is skin and the objective of the analysis is to determine the blood sugar level, then for example, the ball of the thumb, the fingertip, the ball of the hand or other surface of the body is brought into contact with the second surface 12 of the optical medium 10. The body surface to be brought into contact can be prepared in advance, by attaching and then removing a fabric strip to remove dead skin cells, wherein the fabric strip comprises a substance which adheres to the surface of the skin.

Figure 2:
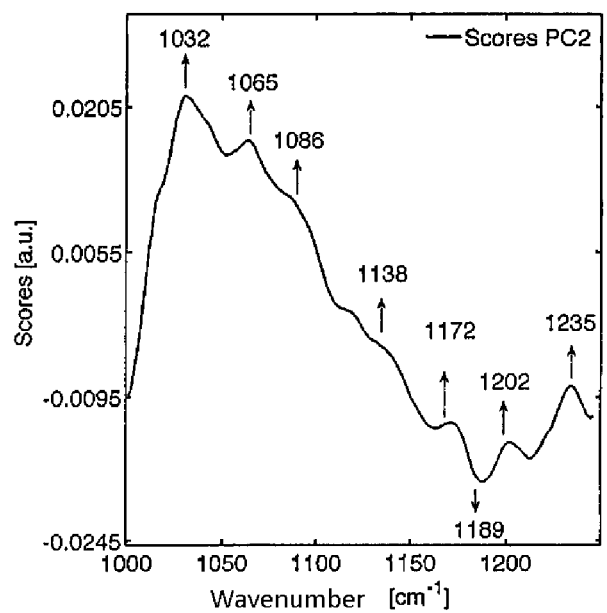
FIG. 2 shows glucose bands which were measured when analyzing human skin with the preferred exemplary embodiment of the system according to the invention.

The spectra of the skin, which were measured in this way with the preferred exemplary embodiment of the system according to the invention, show the bands of keratinocytes and lipids as the first principal component. The second principal component measured were the glucose bands shown in FIG. 2.

Figure 3:
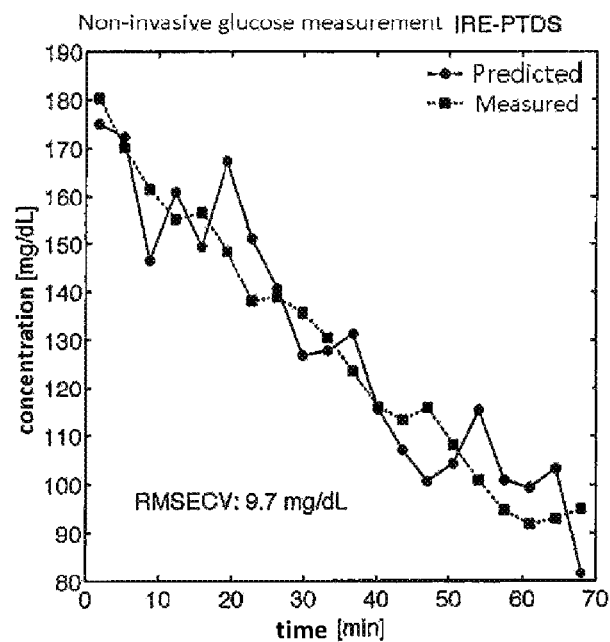
FIG. 3 shows a comparison of the non-invasive determination of the blood glucose level in accordance with the preferred exemplary embodiment of the system according to the invention, with an invasive measurement using a glucometer.

In a comparison between the non-invasive determination of the blood glucose level in accordance with the preferred exemplary embodiment of the system according to the invention and an invasive measurement with a glucometer, a good correspondence was obtained, as shown in FIG. 3, even in the region of low concentration (180 mg/dL to less than 100 mg/dL). FIG. 3 shows the measured blood glucose values and the blood sugar concentration determined from the amplitude of the second principal component.

Figure 4:
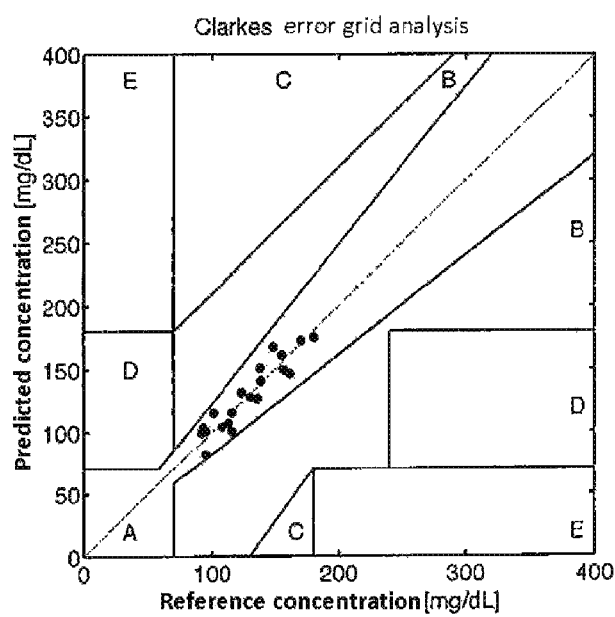
FIG. 4 shows the evaluation of the non-invasive measurement of the glucose level in accordance with FIG. 3 in a Clarke error grid.

If, as shown in FIG. 4, the results of the non-invasive measurement of the blood sugar level as shown in FIG. 3 are plotted in a Clark error grid, all data points of the measurement lie in the "A" zone, in which 90% of the values must lie in an accepted method.

The quantum cascade laser 30 is tuneable in the wavelength range of 8 µm to 11 µm. From the measured absorption spectrum of the glucose in the interstitial fluid, the blood sugar level of the patient is calculated by means of a calibration curve.

In a preferred embodiment the system is permanently attached to the patient, for example in the form of a wrist band, and is additionally configured to alert the patient with a warning signal if the glucose concentration in the interstitial fluid falls below a predetermined value.

In a further preferred embodiment, the system can control an insulin pump, in order to maintain a constant blood sugar value in the patient.

In a further preferred embodiment the computer 52 can be configured to record the intensity measurements as a function of the wavelength or wavelength range of the quantum cascade laser 30, for different pulse frequencies of the infrared laser beam. For this purpose the computer 52 comprises a processor, a storage unit and instructions, which, when they are executed by the processor, record the intensity measurements in association with the wavelength or wavelength range, and the pulse frequency of the infrared laser beam.

Figure 5:
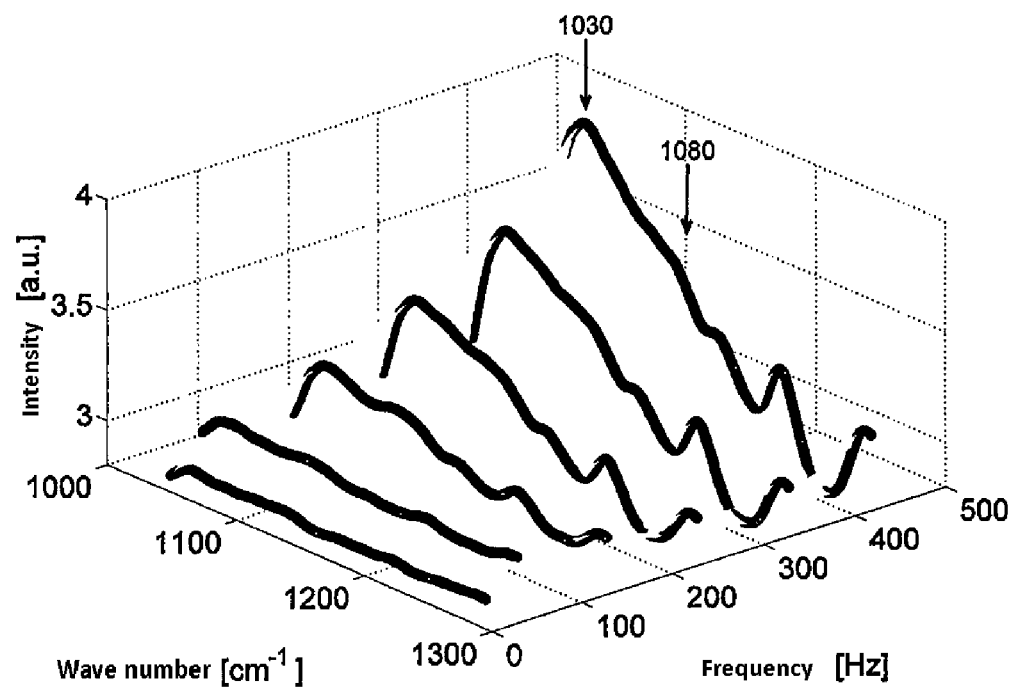
FIG. 5 shows absorption intensity spectra which were obtained with the preferred exemplary embodiment of the system according to the invention at different modulation frequencies.

On this point, FIG. 5 shows intensity measurements, measured with the further preferred embodiment, of the substance arrangement shown in FIG. 6a, consisting of a glucose solution 64 covered with a polymer film 66, which is arranged on the optical medium 10. The comparison of the absorption spectra shown in FIG. 5 with the absorption intensity spectra shown in FIGS. 6b and 6c shows that at higher frequencies, the influence of the absorption by the polymer film 66 on the qualitative profile of the absorption intensity is reduced. By subtraction or division of the absorption intensity spectra at different pulse frequencies, influences of specific layers can thus be largely eliminated, or absorption intensity spectra of specific substance layers can be calculated, so that, for example, a depth profile for the substances present in the substance 100 to be examined can be determined.

The difference formation or division of the spectra can be carried out, for example, as shown in FIG. 5, relative to a specified reference spectrum. The spectrum at the lowest or highest pulse frequency, for example, can be used as a reference spectrum. To take account of different pumping intensities in the respective layers, caused by the absorption of higher layers, the subtraction or division can be preceded by a determination of weighting factors, wherein the spectra or spectral values that are to be subtracted from or divided by one another are to be multiplied by a weighting factor. In addition, a principal component analysis based on the non-linear iterative partial least squares (NIPALS) algorithm can be used, for example for determining a substance which is distributed differently by depth in a solid matrix.

Furthermore, the person skilled in the art will appreciate that the above exemplary embodiments are to be understood as being purely illustrative and in no way restrictive of the scope of protection of the claims. In particular, it should be noted that the specific applications of the system are not intended to be limited to the applications described in the figures. On the contrary, it is assumed that the person skilled in the art will immediately realise that the applications described in the drawings are only intended to clarify the inventive principle, which is applicable to a plurality of different substances and to substances contained therein.

LIST OF REFERENCE NUMERALS

10 Optical medium
11 First surface of the optical medium
12 Second surface of the optical medium
13 Third surface of the optical medium
14 Fourth surface of the optical medium
20 Quantum cascade laser
21 First infrared laser beam partial path
22 Optical chopper 23 Parabolic mirror
24 Second infrared laser beam partial path
25 Third infrared laser beam partial path
30 Probe laser
31 Mirror
40 Photodiode
41 Iris diaphragm
50 Lock-in amplifier
51 Analogue-to-digital converter
52 Computer
60 Alignment laser
61 Mirror
62 Mirror
64 Glucose solution
66 Polymer film

We claim:

1. A method for analyzing a substance, comprising the following steps:
    arranging an optical medium on a substance surface so that at least a portion of the surface of the optical medium is in contact with the substance surface;
    emitting an excitation light beam with an excitation wavelength through the region of the surface of the optical medium in contact with the substance surface onto the substance surface;
    emitting a probe light beam through the optical medium onto the region of the surface of the optical medium which is in direct contact with the substance surface, in such a way that the probe light beam and the excitation light beam overlap at an interface of the optical medium and the substance surface at which the probe light beam is reflected;
    directly or indirectly detecting a deflection of the reflected probe light beam as a function of the wavelength of the excitation light beam; and
    analysing the substance on the basis of the detected deflection of the probe light beam as a function of the wavelength of the excitation light beam,
    wherein the substance is the skin of a patient and the analysis of the substance comprises one of:
    determining a blood sugar level of the patient,
    determining a water content of the skin of a patient,
    determining a protein composition of the skin of the patient, and
    determining a protein composition of the skin of the patient in different skin layers.

2. The method according to claim 1, comprising the further step of:
    aligning the probe light beam such that the probe light beam undergoes total internal reflection at the interface between the optical medium and the substance surface.

3. The method according to claim 1, in which the excitation light beam is an infrared light beam.

4. The method according to claim 1, in which the excitation light beam is an intensity-modulated pulsed excitation light beam.

5. The method according to claim 4, in which the modulation frequency is between 5 and 2000 Hz.

6. The method according to claim 4, wherein the step of emitting the excitation light beam is repeated for different modulation frequencies and the step of analyzing the substance comprises the analysis of the substance on the basis of the detected deflections of the probe beam as a function of the wavelength and the modulation frequency of the excitation light beam.

7. The method according to claim 6, wherein the step of analyzing the substance comprises either (1) a subtraction of a value which is based on a deflection of the probe light beam that was detected at a first modulation frequency, from a value which is based on a deflection of the probe light beam that was detected at a second modulation frequency; or
    (2) a division of a value which is based on a deflection of the probe light beam that was detected at a first modulation frequency, by a value which is based on a deflection of the probe light beam that was detected at a second modulation frequency.

8. The method according to claim 6, wherein the step of analyzing the substance comprises either (1) a subtraction of values based on deflections of the probe light beam that were detected at a first modulation frequency for different wavelengths of the excitation light beam, from values based on deflections of the probe light beam that were detected at a second modulation frequency for different wavelengths of the excitation light beam; or
    (2) a division of values based on deflections of the probe light beam, which were detected at a first modulation frequency for different wavelengths of the excitation light beam, by values based on deflections of the probe light beam, which were detected at a second modulation frequency for different wavelengths of the excitation light beam, wherein the values are preferably spectral absorption intensity values.

9. The method of claim 8, wherein said values based on deflections of the probe light beam that were detected at a second modulation frequency for different wavelengths of the excitation light beam are spectral absorption intensity values.

10. The method according to claim 6, wherein the step of analyzing further comprises associating values based on deflections of the probe light beam, which were detected at different modulation frequencies, with different regions in the substance.

11. The method according to claim 4, in which the excitation light beam is modulated using an optical chopper.

12. The method according to claim 4, in which the detection of the deflection of the probe light beam comprises amplification of an associated measurement signal with a lock-in amplifier.

13. The method according to claim 1, in which the wavelength of the excitation light beam is varied so that:
    the wavelength is cyclically tuned within a predetermined wavelength range, or
    characteristic absorption wavelengths of a suspected substance, are selectively set.

14. The method according to claim 1, wherein the excitation light beam is an excitation laser beam, and/or wherein the probe light beam is a probe laser beam.

15. The method according to claim 1, wherein a polarisation of the probe light beam is set such that the deflection of the reflected probe light beam is a maximum.

16. The method according to claim 1, in which the excitation light beam is generated by means of a quantum cascade laser.

17. The method according to claim 1, in which the excitation wavelength is selected from a range of 6 µm to 13 µm.

18. The method according to claim 1, in which the excitation light beam is focussed on the said surface of the optical medium by means of an optical device comprising a parabolic mirror.

19. The method according to claim 18, in which the optical device is adjusted by means of an alignment laser configured to emit visible light.

20. The method according to claim 1, in which the wavelength of the probe light beam is in the visible range.

21. The method according to claim 1, in which the deflection of the probe light beam
is determined by means of a photo-detector, which is arranged behind an iris diaphragm, or
is determined by means of a PSD.

22. The method according to claim 1, in which before the detection of the deflection, the probe light beam is reflected back into an overlap region with the excitation light beam on the interface at least one additional time.

23. The method according to claim 1, wherein the substance is the skin of a patient, and the method comprising the additional step of:
preparing the surface of the skin by attaching and removing a fabric strip to remove dead skin cells,
wherein the fabric strip comprises a material which adheres to the surface of the skin.

24. A method for analyzing a substance, comprising the following steps:
arranging an optical medium on a substance surface so that at least a portion of the surface of the optical medium is in contact with the substance surface;
emitting an excitation light beam with an excitation wavelength through the region of the surface of the optical medium in contact with the substance surface onto the substance surface;
emitting a probe light beam through the optical medium onto the region of the surface of the optical medium which is in direct contact with the substance surface, in such a way that the probe light beam and the excitation light beam overlap at an interface of the optical medium and the substance surface at which the probe light beam is reflected;
directly or indirectly detecting a deflection of the reflected probe light beam as a function of the wavelength of the excitation light beam; and
analysing the substance on the basis of the detected deflection of the probe light beam as a function of the wavelength of the excitation light beam,
wherein the substance:
is a flowing or stationary fluid or emulsion and the analysis of the substance comprises determining a sugar content, alcohol content, fat and/or protein content of the fluid;
is a fuel and the analysis of the substance comprises determining an alcohol content, rapeseed oil methyl ester content, lead or benzene content of the fuel;
is fresh or salt water and the analysis of the substance comprises determining a contamination of the water; or
is a body fluid.

25. A method for analyzing a substance, comprising the following steps:
arranging an optical medium on a substance surface so that at least a portion of the surface of the optical medium is in contact with the substance surface;
emitting an excitation light beam with an excitation wavelength through the region of the surface of the optical medium in contact with the substance surface onto the substance surface;
emitting a probe light beam through the optical medium onto the region of the surface of the optical medium which is in direct contact with the substance surface, in such a way that the probe light beam and the excitation light beam overlap at an interface of the optical medium and the substance surface at which the probe light beam is reflected;
directly or indirectly detecting a deflection of the reflected probe light beam as a function of the wavelength of the excitation light beam; and
analysing the substance on the basis of the detected deflection of the probe light beam as a function of the wavelength of the excitation light beam, in which, based on the detected deflection of the probe light beam, an absorption intensity value is associated with the wavelength of the excitation light beam, and
wherein the analysis of the substance comprises determining the blood sugar level of a patient and wherein the absorption intensity value is compared with a calibration absorption intensity value, which represents the absorption intensity value of the skin of the patient at a known blood sugar level and at this exact wavelength of the excitation light beam.

26. The method according to claim 25, wherein the current blood sugar level of the patient is determined on the basis of the comparison, wherein the determined blood sugar level deviates the more from the blood sugar level during calibration, the more the absorption intensity value deviates from the calibration absorption intensity value.

27. An apparatus for determining blood sugar level of a patient, which comprises the following:
a system for analysing a substance, comprising:
an optical medium;
a device for emitting an excitation light beam with an excitation wavelength,
wherein the device for emitting the excitation light beam is arranged such that the emitted excitation light beam enters the optical medium and exits the same again at a predetermined point on the surface of the optical medium; and
a measurement device, wherein the measurement device comprises a device for emitting a probe light beam, which is arranged such that an emitted probe light beam enters the optical medium, and during operation the probe light beam and the excitation light beam overlap at an interface of the optical medium and a substance surface at which the probe light beam is reflected,
and wherein the measurement device comprises a device for receiving the reflected probe light beam and for directly or indirectly detecting a deflection of the reflected probe light beam,
a controller for setting different wavelengths of the excitation light beam, and
a logic unit or calculating unit, which is configured to determine blood sugar levels in the skin of a patient from detected deflections of the probe light beam as a function of the excitation wavelength, when the optical medium is brought into contact with the skin of the patient in such away that the excitation light beam emerging from the optical medium at the said predetermined point enters into the skin.

28. The apparatus according to claim 27, wherein the probe light beam in operation undergoes total internal reflection at the interface between the optical medium and the substance surface.

29. The apparatus according to claim 27, wherein the excitation light beam is an infrared light beam.

30. The apparatus according to claim 27, wherein the excitation light beam is an intensity-modulated, in particular pulsed, excitation light beam,
wherein the device for receiving the reflected probe light beam and for directly or indirectly detecting a deflection of the reflected probe light beam comprises a lock-in amplifier.

31. The apparatus according to claim 30, in which the modulation frequency is between 5 and 2000 Hz.

32. The apparatus according to claim 30, further comprising an optical chopper positioned in the beam path of the excitation light beam suitable for modulating the intensity of the excitation light beam.

33. The apparatus according to claim 27, wherein the excitation light beam is an excitation laser beam and the device for emitting the excitation light beam is configured for emitting excitation laser beams of different excitation frequencies.

34. The apparatus according to claim 27, having an optical device which is suitable for focussing the excitation light beam on the predetermined point, wherein the optical device comprises a parabolic mirror.

35. The apparatus according to claim 34, further comprising an alignment laser for aligning the optical device.

36. The apparatus according to claim 27, in which the device for emitting the excitation light beam is a quantum cascade laser.

37. The apparatus according to claim 27, in which the device for emitting the excitation light beam is tunable in an excitation wavelength range of 6 μm to 13 μm.

38. The apparatus according to claim 27, in which the wavelength of the probe light beam is in the visible range.

39. The apparatus according to claim 27, wherein the device for receiving the reflected probe light beam and for directly or indirectly detecting a deflection of the reflected probe light beam
comprises a photo-detector including a photodiode and an iris diaphragm, wherein the photo-detector is arranged behind the iris diaphragm, or
comprises a PSD.

40. The apparatus according to claim 27, in which before the detection of the deflection, the probe light beam is reflected back into a region of overlap with the excitation light beam on the interface at least one additional time.

41. The apparatus according to claim 27,
wherein the excitation light beam is an intensity modulated light beam, said apparatus further comprising:
a controller for setting different modulation frequencies of the excitation light beam, and
a logic unit or calculating unit, which is configured to analyze the substance by means of detected deflections of the probe light beam at different modulation frequencies, when the optical medium is brought into contact with the substance in such a way that the excitation light beam emerging from the optical medium at the said predetermined point enters into the substance.

42. The apparatus for analyzing a substance according to claim 41, wherein the substance is said skin of said patient, and the logic unit or calculating unit is configured to analyze different layers of the skin of the patient from detected deflections of the probe light beam at different modulation frequencies.

43. An apparatus for analyzing constituents of a liquid or emulsion, comprising the following:
a system for analysing a substance, comprising:
an optical medium;
a device for emitting an excitation light beam with an excitation wavelength,
wherein the device for emitting the excitation light beam is arranged such that the emitted excitation light beam enters the optical medium and exits the same again at a predetermined point on the surface of the optical medium; and
a measurement device, wherein the measurement device comprises a device for emitting a probe light beam, which is arranged such that an emitted probe light beam enters the optical medium, and during operation the probe light beam and the excitation light beam overlap at an interface of the optical medium and a substance surface at which the probe light beam is reflected,
and wherein the measurement device comprises a device for receiving the reflected probe light beam and for directly or indirectly detecting a deflection of the reflected probe light beam,
a controller for setting different wavelengths of the excitation light beam, and
a logic unit or calculating unit, which is configured to determine constituents of the liquid or emulsion from detected deflections of the probe light beam as a function of the excitation wavelength, when the optical medium is brought into contact with the liquid or emulsion in such a way that the excitation light beam emerging from the optical medium at the said predetermined point enters into the liquid or emulsion.

44. A method for analyzing a substance, comprising the following steps:
arranging an optical medium on a substance surface so that at least a portion of the surface of the optical medium is in contact with the substance surface;
emitting an excitation light beam with an excitation wavelength through the region of the surface of the optical medium in contact with the substance surface onto the substance surface;
emitting a probe light beam through the optical medium onto the region of the surface of the optical medium which is in direct contact with the substance surface, in such a way that the probe light beam and the excitation light beam overlap at an interface of the optical medium and the substance surface at which the probe light beam is reflected;
directly or indirectly detecting a deflection of the reflected probe light beam as a function of the wavelength of the excitation light beam; and
analysing the substance on the basis of the detected deflection of the probe light beam as a function of the wavelength of the excitation light beam, wherein the excitation light beam is an intensity-modulated pulsed excitation light beam, wherein the step of emitting the excitation light beam is repeated for different modulation frequencies and the step of analyzing the substance comprises the analysis of the substance on the basis of the detected deflections of the probe beam as a function of the wavelength and the modulation frequency of the excitation light beam, wherein the step of analyzing the substance comprises either (1) a subtraction of a value which is based on a deflection of the probe light beam that was detected at a first modulation frequency, from a value which is based on a deflection of the probe light beam that was detected at a second modulation frequency; or
(2) a division of a value which is based on a deflection of the probe light beam that was detected at a first modulation frequency, by a value which is based on a deflection of the probe light beam that was detected at a second modulation frequency.

* * * * *

UNITED STATES PATENT AND TRADEMARK OFFICE
CERTIFICATE OF CORRECTION

| | | |
|---|---|---|
| PATENT NO. | : 10,883,933 B2 | Page 1 of 1 |
| APPLICATION NO. | : 15/319426 | |
| DATED | : January 5, 2021 | |
| INVENTOR(S) | : Mäntele et al. | |

It is certified that error appears in the above-identified patent and that said Letters Patent is hereby corrected as shown below:

In the Claims

In Column 16, Line 52:
Replace "away" with --a way--

In Column 17, Lines 40-41:
Replace "intensity modulated" with --intensity-modulated--

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*